(12) United States Patent
Bonan et al.

(10) Patent No.: US 8,868,170 B2
(45) Date of Patent: Oct. 21, 2014

(54) ACTIVE MEDICAL DEVICE, INCLUDING AN IMPLANTABLE DEFIBRILLATOR, FOR DETECTION OF QRS COMPLEXES IN A VERY NOISY SIGNAL

(75) Inventors: José Bonan, Paris (FR); Christophe Harmel, Sceaux (FR)

(73) Assignee: Sorin CRM S.A.S., Clamart Cedex (FR)

(*) Notice: Subject to any disclaimer, the term of this patent is extended or adjusted under 35 U.S.C. 154(b) by 256 days.

(21) Appl. No.: 13/448,191

(22) Filed: Apr. 16, 2012

(65) Prior Publication Data

US 2013/0261478 A1 Oct. 3, 2013

(30) Foreign Application Priority Data

Apr. 15, 2011 (FR) .................................... 11 53301

(51) Int. Cl.
  *A61B 5/04* (2006.01)
  *A61B 5/0456* (2006.01)
  *A61B 5/00* (2006.01)

(52) U.S. Cl.
  CPC ................ *A61B 5/0456* (2013.01); *A61B 5/7203* (2013.01)
  USPC ............................ 600/521; 600/517; 600/516

(58) Field of Classification Search
  CPC ... A61B 5/0456; A61B 5/0452; A61B 5/7203
  USPC ........................................ 600/521, 516, 517
  See application file for complete search history.

(56) References Cited

U.S. PATENT DOCUMENTS

| | | | |
|---|---|---|---|
| 4,000,461 A | 12/1976 | Barber et al. | |
| 5,010,887 A | * 4/1991 | Thornander | 600/509 |
| 5,836,980 A | 11/1998 | Legay | |
| 6,161,037 A | 12/2000 | Cohen | |
| 2007/0282379 A1 | 12/2007 | Limousin et al. | |

FOREIGN PATENT DOCUMENTS

| | | |
|---|---|---|
| EP | 0429025 A2 | 5/1991 |
| EP | 0775502 A1 | 5/1997 |
| EP | 0958843 A1 | 11/1999 |
| EP | 1857142 A1 | 11/2007 |

OTHER PUBLICATIONS

Foreign Search Report (Annexe Au Rapport De Recherche Preliminaire Relatif a La Demande De Brevet Francais No. FR 1153301 FA 750005), Jul. 28, 2011.

* cited by examiner

*Primary Examiner* — Christopher D Koharski
*Assistant Examiner* — Philip Edwards
(74) *Attorney, Agent, or Firm* — Foley & Lardner LLP

(57) ABSTRACT

An active implantable medical device (e.g., implantable pacemaker or defibrillator), for detection of QRS complexes in noisy signals. Functional units (12-16) collect, amplify, prefilter and convert from analog-to-digital an endocardial signal, and digital functional units (18) provide signal processing and analysis of the digitized signal, for delivery of an indicator corresponding to a signal peak detection representative of the presence of a QRS complex in the endocardial signal. A double threshold comparator (30) is employed, receiving as input (28) the digitized signal and outputting (40) the indicator of peak detection when, cumulatively: the amplitude (A) of the input signal exceeds a peak amplitude threshold (SA), and the peak amplitude threshold is exceeded for a period (W) greater than a peak width threshold (SW). The peak amplitude threshold (SA) is a variable adaptive threshold, according to a noise level calculated from the energy (RMS) of the input signal.

6 Claims, 3 Drawing Sheets

ACTIVE MEDICAL DEVICE, INCLUDING AN IMPLANTABLE DEFIBRILLATOR, FOR DETECTION OF QRS COMPLEXES IN A VERY NOISY SIGNAL

RELATED APPLICATIONS

The present application claims the priority date benefit of French patent application Ser. No. 11/53301 entitled "Active medical device, including an implantable defibrillator, for detection of QRS complexes in a very noisy signal" and filed Apr. 15, 2011, which is hereby incorporated by reference in its entirety.

FIELD

The present invention is directed to "active implantable medical devices" as defined by the 20 Jun. 1990 Directive 90/385/EEC of the Council of European Communities, more particularly to devices that continuously monitor a patient's heart rhythm and delivers to the heart, if necessary, an electrical pulse for cardiac stimulation, resynchronization and/or a defibrillation, in response to a detected cardiac arrhythmia.

BACKGROUND

Cardiac rhythm analysis is commonly performed from electrogram signals (EGM) collected by electrodes located on endocardial leads implanted in the myocardium to measure the atrial and/or ventricular depolarization potential. These EGM signals are analyzed by the device, which delivers to the patient if necessary an appropriate therapy in the form of low energy stimulation pulses (for bradycardia pacing or resynchronization of the ventricles) or high energy defibrillation shocks.

The cardiac rhythm analysis, and therefore the decision whether or not to deliver a therapy, however, can be affected by artifacts collected by the endocardial lead. These artifacts can have various origins. A first series of artifacts corresponds to situations where the device not only detects the cardiac event itself, e.g., a wave of depolarization of the cavity in question, but also a disturbance associated with this event and wrongly considered as another depolarization event that occurred after the first, for example, a late depolarization wave, crosstalk detected between different heart cavities, and far-field signal detection.

A second series of artifacts, which are the subject of the present invention, are the artifacts from extrinsic noise and not related to a depolarization of the myocardium. This noise can have many origins, including, for example, the myopotentials associated with muscle contractions, electromagnetic interference (EMI) from electronic surveillance equipment, electrical devices located nearby, electrosurgical instruments, communication systems, and the like.

In addition, the digital signal processing ("DSP") units typically used in active implantable medical device generate a certain noise level, which is added to the signal depolarization. In particular, the digital filtering can initially increase the amplitude of the signal oscillations before the amplitude slowly decreases as the system stabilizes over time, with the consequence of disrupting the analysis carried out downstream of this distorted signal.

In general, a noise that is present with varying regularity, whether extrinsic or due to the specific digital processing, can be interpreted by the device as a depolarization of the myocardium, with the risk of generating inappropriate therapy, such as wrongly inhibiting the bradycardia pacing or the resynchronization pacing, or conversely, by falsely delivering inappropriate shocks.

Various techniques have been proposed to reduce the impact of extrinsic noise, including the upstream application to the signal processing circuits for analog or digital filtering, the introduction of refractory periods, the automatic adjustment of the sensitivity of the detection amplifiers, or the automatic gain control of these amplifiers.

EP 0958843 A1 describes one technique of "autosensing", wherein an algorithm continuously adapts the detection threshold depending on the level of noise and the amplitude of the EGM signals associated with detected cardiac events. However, the use of these autosensing methods is always at the expense of a good detection. In particular, to detect ventricular fibrillation (VF), the signal level of which is considered relatively low, it is necessary to have a maximum sensitivity, in order to prevent failing to detect events that should have been detected. But the signal amplitude of ventricular fibrillation (specifically, QRS complexes indicative of ventricular depolarizations) may be of a variable level, between the noise signal level and the signal level corresponding to a sinus complex (a spontaneous depolorization).

Consequently, setting a threshold low enough to detect ventricular fibrillation runs the inevitable risk of also detecting a possible noise. If in addition there is a regular noise, for a patient with normal sinus heart rhythm, this noise can be confused with depolarizations. This may distort the evaluation of the average cardiac rate as determined by the device, with an (incorrectly) estimated rate of a level much higher than reality, and a corresponding risk of applying undesirable antitachycardia therapy (a false positive situation, called "oversensing").

Conversely, if the device is programmed to a too low sensitivity value, that is to say, with a too high detection threshold, the actual episodes of ventricular fibrillation may not be detected (a false negative situation, called "undersensing") with potentially serious consequences for the patient.

With the detection of extrinsic noise being usually inevitable, the problem addressed by the present invention is to distinguish these noises from the actual heart depolarizations, in order to avoid triggering inappropriate therapies and, conversely, inhibiting delivery of therapies that if delivered would have been appropriate.

The identification of these noises and their mitigation by means of filters is a complex task, the main difficulty being the extreme variability of these spurious signal components, which implies relatively complex processing to be effective.

Complex digital processing techniques have been proposed for this purpose to ensure the detection of a QRS complex in the endocardial signal, including, for example, non-linear filtering, wavelet transform, artificial network, genetic algorithm and linear prediction techniques. These various, complex, algorithms require a large number of arithmetic operations and require significant computing resources, with a further significant increase in energy consumption by the device, consequently having an impact on the useful life of the implanted device.

Another technique, described, for example, in EP 0775502 and its counterpart U.S. Pat. No. 5,836,980 (both assigned to Sorin CRM S.A.S, previously known as ELA Medical), is to analyze the signal characteristics by deriving it by differentiating means to assess the instantaneous variations of the signal by comparing them to predetermined thresholds. The required circuits are relatively simple but, however, they enable a relatively limited discrimination in the case of highly noisy signals.

Yet another technique was proposed by EP 1857142 A1 and its counterpart U.S. Pat. Publication No. 2007/0282379 (both assigned to Sorin CRM S.A.S., previously known as ELA Medical), which is to conduct a double detection by analysis of the depolarization of the EGM electrical signal, and of the contraction of the myocardium by measuring the endocardial acceleration (EA), the latter obtained via an accelerometer in direct contact with the heart muscle. In the presence of noises, the device operates an alarm verification to confirm that the detected signal has actually been followed by a mechanical activity of the heart and thus constitutes a signal of depolarization (QRS complex) and not an artifact. In this regard, the depolarization is an electrical phenomenon sensitive to noise and is indeed usually followed by cardiac contraction, a mechanical phenomenon that is not affected by the same noise.

But this presupposes to have a lead equipped with an endocardial acceleration sensor, and if the patient already has an implanted device, implies during a change in the generator to change not only the generator but also the lead, which is a much more difficult surgery.

EP 0429025 A2 describes a technique to make a double discrimination, both on the amplitude and on the width of the peaks of detected signal: a first amplitude discrimination is used to extract only signals exceeding a given level, while the analysis of the width of the signal being above this threshold amplitude discriminates a possible parasitic component that would not have been eliminated in the filtering upstream of this processing. U.S. Pat. No. 4,000,461 describes a comparable technique of discrimination by amplitude/duration cross-analysis of the peaks of detected signal. The thresholds for comparison (amplitude and width) are adjustable, and adjusted to a value chosen by the practitioner during the programming of the device. This presupposes, however, that the conditions at the time of adjustment remain fairly constant over time, for an effective discrimination. But in practice this is rarely the case, making this technique unreliable for detecting the presence (or not) of a QRS complex in the received endocardial signal, especially to detect ventricular fibrillation for which, as explained above, the useful signal can be at a variable level, intermediate between the noise and the signals of the sinus complexes. Because of the fixed parameters, the risks of oversensing or undersensing are then particularly high, with the potential serious consequences that have been outlined above.

OBJECTS AND SUMMARY

It is, therefore, an object of the present invention is to provide an endocardial signal processing to effectively discriminate spurious noise components to reliably detect the presence (or not) of a QRS complex in the collected endocardial signal.

It is another object of the present invention to provide such endocardial signal processing with reduced need for computing power for digital processing, resulting in a preservation of the battery power and useful life of the implantable device.

It is yet another object of the present invention to propose such an endocardial signal processing that can be used regardless of the type of lead used, this feature being particularly advantageous when replacing only the generator of the implantable device without replacing the lead(s) already present.

The present invention is broadly directed to providing a double discrimination threshold (amplitude and duration of the peak), but wherein the amplitude threshold for discriminating between signal and noise is a variable, adaptive threshold, updated based on the average noise level determined in the absence of detected depolarization signals. Preferably the discrimination amplitude threshold is regularly updated according to the level exceeding the threshold.

One aspect of the present invention is for a device of the generic type disclosed in EP 0429025 A2 above, namely an active implantable medical device having circuits for collecting, amplifying, prefiltering and analog-to-digital conversion of a collected endocardial signal, and digital signal processing circuits for analyzing the digitized endocardial signal, for delivering an indicator corresponding to a detection of a signal peak representative of a QRS complex present in the endocardial signal. The digital processing and analysis circuits have a dual threshold for the comparator, receive as input the digitized signal, and output the indicator for a peak detection when, cumulatively: the amplitude of the input signal exceeds a peak amplitude threshold, and the peak amplitude threshold, and the peak width threshold.

In one embodiment of the present invention, the peak amplitude threshold is a variable adaptive threshold, and the digital processing and analysis circuit further comprises means for determining a peak amplitude threshold, by combining a predetermined base threshold value and a variable noise level of the input signal, and means for determining a variable noise level value from the noise present in the digitized input signal, outside of the periods of detection of signal peak.

In a preferred embodiment, the means for determining the value of the variable noise level comprises means for calculating the energy of the input signal over a predetermined calculation period during which the amplitude of the input signal does not exceed said peak amplitude threshold. In a more preferred embodiment, the device may further include means for inhibiting and resetting the means for determining the variable noise level value, in response to a crossing of said peak amplitude threshold before expiry of the predetermined calculation period.

The peak width threshold is preferably a fixed, predetermined threshold.

Advantageously, the digital processing and analysis circuits also include a low pass filter for filtering the input signal, as well as a high-pass filter and a rectifier, to filter and rectify the signal applied to the low pass filter.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which.

DETAILED DESCRIPTION

An example of a preferred embodiment of a device of the present invention will now be described with reference to the drawings FIGS. 1-3.

As regards its software aspects, the present invention can be implemented by an appropriate programming of the control software instructions of a known device, for example, a cardiac pacemaker or a defibrillator/cardioverter, including circuits for collecting a signal provided by endocardial leads and/or one or more implanted sensors. The present invention may particularly be applied to implantable devices such as those of the Reply and Paradym device families produced and marketed by Sorin CRM, Clamart France, formerly known as ELA Medical, Montrouge, France.

These devices include signal conditioning circuits and programmable microprocessor circuitry including central processing units, registers and memory able to receive, format, and process electrical signals collected (detected) by implanted electrodes and to deliver electrical pulses to these electrodes for stimulation, cardioversion and/or defibrillation. It is possible to transmit by known telemetry technology software instructions that will be stored in a memory of the implantable device and executed to implement the functions of the present invention that will be described herein. The adaptation of these known devices to implement the functions and features of the present invention is believed to be within the abilities of a person of ordinary skill in the art, and therefore will not be described in detail.

Also, it should be understood that the present invention is preferably implemented by use of software instructions, with appropriate algorithms executed by a microcontroller or alternatively a digital signal processor. For the sake of clarity, the various processing features of present invention to be applied are decomposed and represented by a number of different functional blocks in the form of interconnected "circuits", but this representation is only illustrative, however, and these "circuits" including common elements and corresponding in practice to a plurality of functions generally may be performed by the same software.

Figure 1:
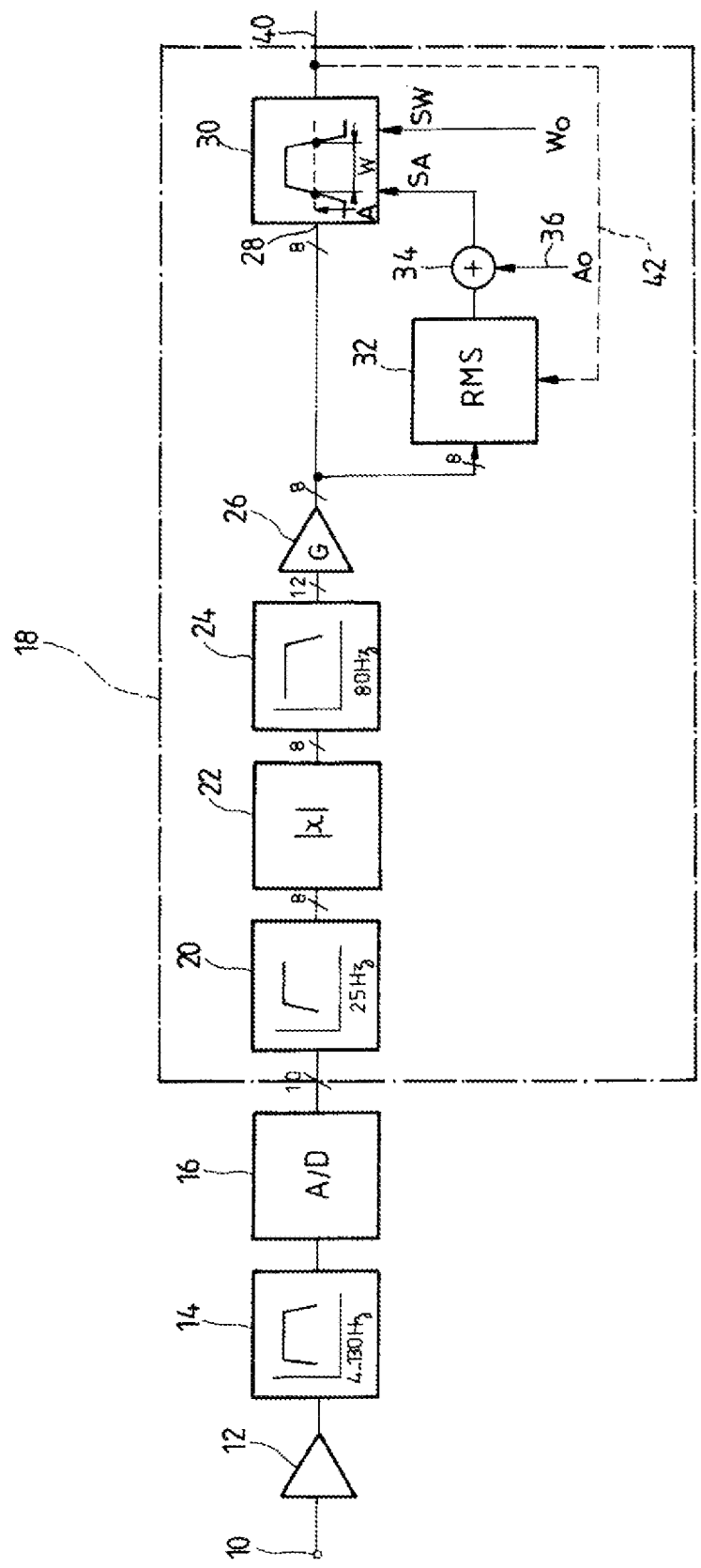
FIG. 1 is a block schematic diagram for detecting the QRS complexes in accordance with a preferred embodiment of the present invention.

FIG. 1 illustrates in the form of functional blocks, one embodiment of the different elements for the detection of the QRS complex of a ventricular depolarization signal, especially in the case of ventricular fibrillation, from an endocardial signal collected by the electrode located at the termination of a lead connected to the generator incorporating this detection circuit.

This system includes an analog part followed by a digital part.

First, the endocardial EGM signal is applied to the input 10 of amplifier 12 and of an analog bandpass filter 14, such as a Butterworth filter, defined by relatively wide limits (typically between 4 and 130 Hz). The amplified and filtered signal is then input to an analog-to-digital converter 16, for a conversion, for example, to 10 bits, at a sampling frequency of 512 Hz.

The digitized raw signal is processed by the digital block 18, in order to detect the presence of a QRS complex. The digitized signal from converter 16 is applied to a high-pass filter 20 so as to eliminate any DC component that may be present (and thus avoid saturation of downstream processing circuits), and also to enhance certain characteristic components of the EGM signal. This high-pass filter 20 is preferably, for example, a third order Butterworth filter with a cutoff frequency of 25 Hz. Such a filter provides a rapid stabilization of the output signal with few oscillations (for a level signal applied to the input). It also has the advantage of consuming relatively little power and not being very demanding in terms of computing resources. The filter may involve converting the ten bit input digital values to an eight bit value, e.g., to limit the dynamic range of the signal.

The next stage is a rectifier 22, which transforms the digitized signal to all positive values and thereby simplifies the subsequent arithmetic operations. While this feature introduces non-linearities, it simplifies further processing (for example, needing only to evaluate positive thresholds when evaluating the amplitude of the signal), and provides greater flexibility and simplification of decision rules of the presence (or not) of a QRS complex.

The rectifier 22 is followed by a low pass filter (24) for increasing the resolution width of the rectified and filtered signal, e.g., converting the eight bit digital values into twelve bit values, to increase the accuracy of the rectifier and filter. This is because, as shall be discussed later, the analysis of this signal implies a width analysis of the signal peaks that were detected, to increase the efficiency of the discrimination compared to the noise. Low-pass filter 24 is preferably, for example, a second order Butterworth filter with a cutoff frequency of about 80 Hz, and preferably a digital filter with infinite impulse response (IIR), which has a relatively low response time. A quick filter provides for the possibility to start the algorithm for QRS detection faster.

The signal thus filtered at the output of filter 24 is then applied at the input of a gain stage 26, the value of which is chosen so as not to saturate the system downstream. The gain stage may involve converting the twelve bit digital values to eight bit values, e.g., to limit the dynamic range of the signal. The resulting signal is applied to the input 28 of a comparator 30, which is preferably a dual threshold comparator of amplitude and of width.

Comparator 30 first analyzes the amplitude A of the signal compared to the amplitude threshold SA and, when the amplitude threshold SA is crossed, analyzes the width W of the amplitude peak compared to the width threshold SW. In other words, for the comparator to switch the indicator from a first state (e.g., a logical low value such as "0") to a second state (e.g., a logical high value such as "1") to indicate the presence of a QRS complex detection, it is necessary that both the amplitude A of the signal exceeds the threshold SA, and that this threshold SA is exceeded for a period W (peak width) greater than the width threshold SW.

The width threshold SW is preferably a predetermined value $W_0$, fixed or set.

However, the amplitude threshold SA is a variable threshold, one that is adaptive depending on the average noise level during a given period. The adaptive amplitude threshold SA is determined by a circuit 32 that determines the noise level. Circuit 32 receives as input the same digital signal as that applied to the input of comparator 30, but only during the periods when it does not exceed the amplitude threshold SA. The noise level is, for example, determined from measure of the energy, more preferably the root mean square (RMS) based on a series of samples during a predetermined calculation period $T_{RMS}$. For reasons of economy of energy consumption, the calculation of RMS is preferably limited to a relatively short duration, such as $T_{RMS}=32$ ms.

The RMS average value obtained is added by an adder 34 to a predetermined base threshold $A_0$ applied as input 36 of adder 34. The resulting value $SA=A_0+RMS$ is applied to the input of the comparator 30 as a reference value of the amplitude threshold SA.

Circuit 32 for calculating the RMS is, as indicated by dashed line 42, coupled to the output 40 of the comparator 30 so as to calculate the RMS value only in certain signal conditions, as is described below.

In summary, the present invention proposes, after prior conditioning of the digitalized signal by appropriate filtering, to operate on the input signal, a selection based on energy between the noise peaks and the useful signal peaks. In other words, the detection of a peak by means of a dual threshold comparator (amplitude and width) offers the possibility to decorrelate the useful signal and the noise and to determine, under certain conditions (see, for example, the explanations given below with reference to FIG. 3), the triggering of the RMS average value associated with the signal. This value, calculated during a certain time duration combined with a predetermined threshold value, and thus allows a regular updating of the amplitude threshold.

Figure 2:
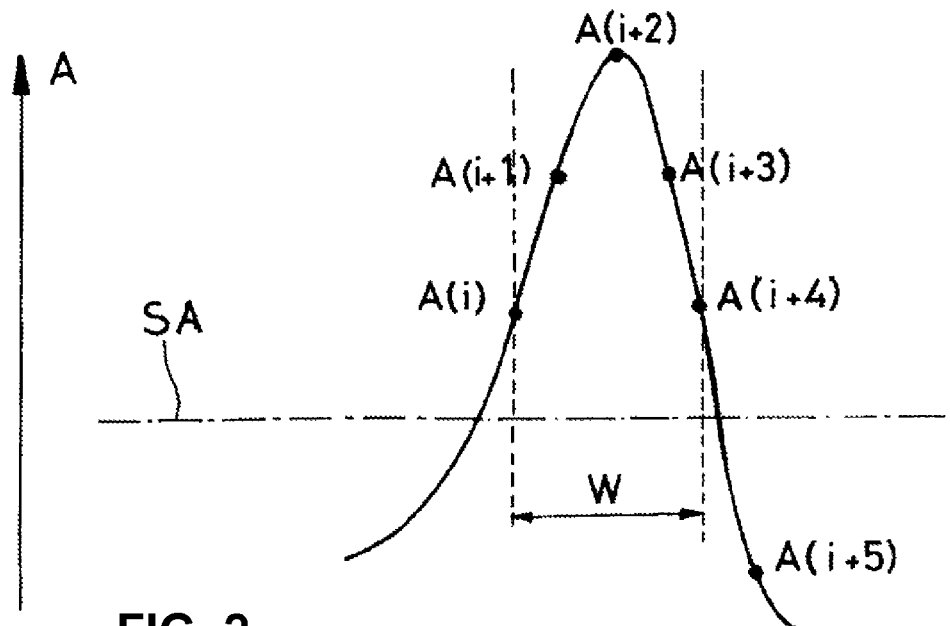
FIG. 2 illustrates graphically a double detection, in amplitude and in width, of the input signal of FIG. 1.

Referring to FIG. 2, a form of filtered digitized signal as applied at the input of the dual-stage comparator 30 is illustrated. This signal is in the form of a succession of discrete samples $A_i, A_{i+1}, A_{i+2}, \ldots$.

Comparator 30 detects first the samples having an amplitude greater than the amplitude threshold SA. If the width W of the signal peak (i.e., the portion of the signal that exceeds the threshold SA) exceeds a width threshold SW (that is, if the number of consecutive samples above the threshold SA exceeds a given number), then the signal peak is considered to represent an actual QRS complex. In other words, if the two thresholds of amplitude and width are cumulatively exceeded, the device considers that there is actual presence of a ventricular depolarization.

As noted above, the width threshold SW is a fixed threshold $W_0$, which is configurable, while the amplitude threshold SA is a variable, adaptive, threshold which varies with the noise level of the analyzed signal, this noise being composed of all the random noise not representative of fluctuations associated with the cardiac depolarization.

Figure 3:
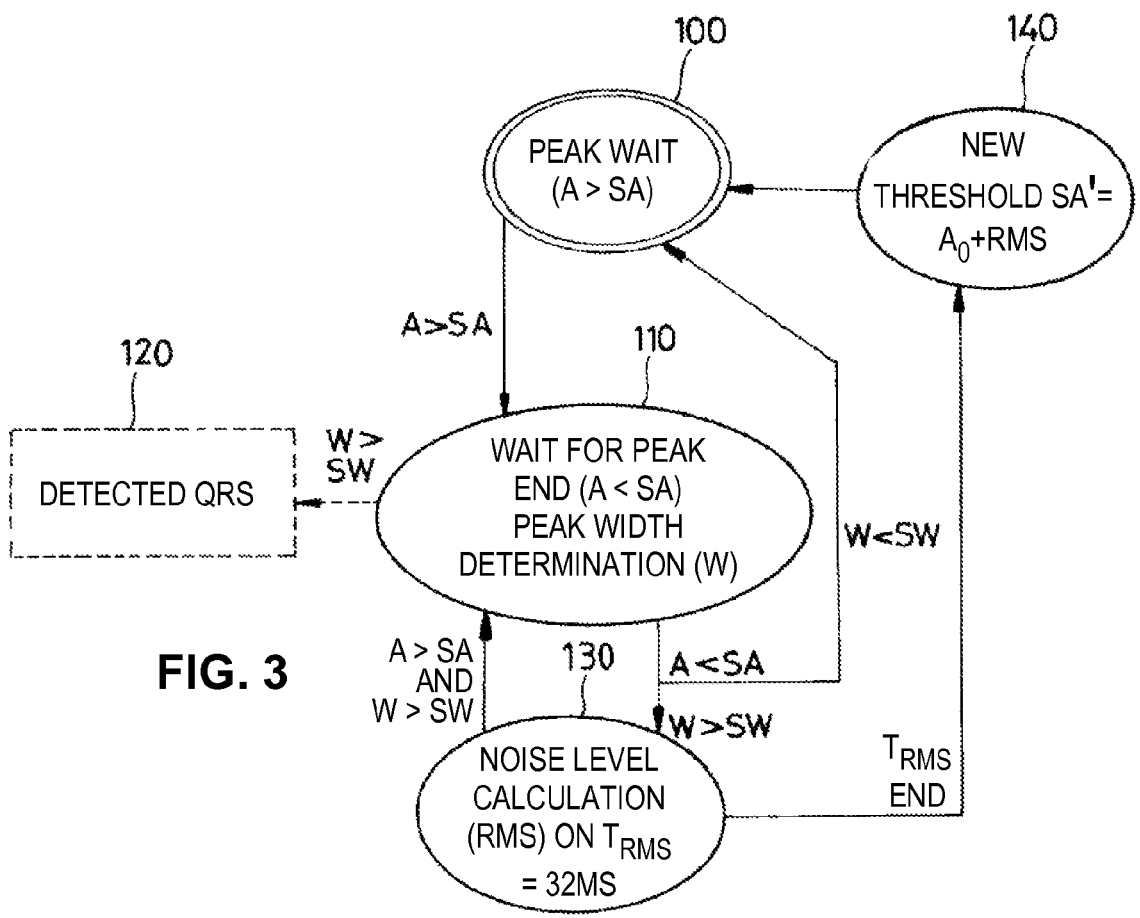
FIG. 3 is a machine sequence state diagram illustrating the different states of the analysis and update algorithm of the adaptive threshold according to the invention.

FIG. 3 illustrates in the form of a state machine diagram the sequence of the different steps of the algorithm for i) the detection of QRS, ii) the calculation of noise level, and iii) the update of the amplitude threshold.

Initially (block 100), the device is waiting for a peak detection, more specifically, waiting for a sample having an amplitude that exceeds the amplitude threshold SA (A>SA).

If such a peak is detected, the machine state changes (block 110) to wait until the detection of the end of the peak (namely, detection of the first of the subsequent samples having an amplitude A that falls below the amplitude threshold level SA). The width W of the peak is then determined (this width corresponding to the number of consecutive samples having amplitude A above the amplitude threshold SA). If this width W is greater than the width threshold SW, then it is considered that the QRS complex was actually detected (block 120). If not, the algorithm returns to block 100.

When the sample amplitude A falls below the threshold SA (A<SA), the algorithm starts calculating the noise level (block 130). This calculation is made over a given period $T_{RMS}$ (e.g., $T_{RMS}$=32 ms), provided that the sample amplitudes A remain below the threshold SA, otherwise, the algorithm cancels the calculation of noise level and returns to block 110. In the latter circumstance, if the sample amplitude A is above the threshold SA, it is considered that a new peak has been detected and will be analyzed, and the time the amplitude was below the threshold SW was less than $T_{RMS}$ and not long enough for the calculation of noise.

If the period $T_{RMS}$ has fully elapsed with the sample amplitude A remaining below the threshold SA, then this threshold is updated (block 140). The new threshold SA' is calculated with the new updated value of the RMS noise (SA'=SA+RMS).

FIGS. 4a to 4d show four different configurations of the analyzed signal applied to the input of the dual-threshold comparator, to illustrate the corresponding actions taken as appropriate.

Figure 4A:
FIGS. 4a to 4d show various possible wave depolarization configurations, to illustrate detection of the QRS complex and for the update of the amplitude threshold in accordance with the present invention.

FIG. 4a illustrates a signal having an amplitude A that always remains below the threshold SA: In this case, the output of the dual threshold comparator 30 remains '0' (corresponding to an "absence of detected QRS"), and the value of the threshold SA remains unchanged. No calculation of noise level is triggered.

Figure 4B:
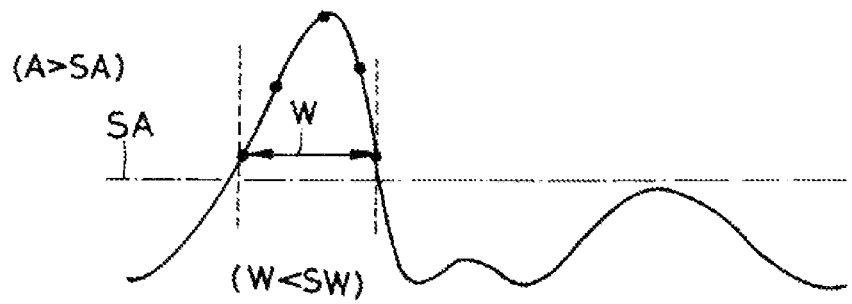

FIG. 4b illustrates a signal having an amplitude A that exceeds the threshold SA, but over a period (width W) below the required width threshold SW. In this case, the detected peak is likely a noise spurious peak, and no action is taken, as in the previous case.

Figure 4C:
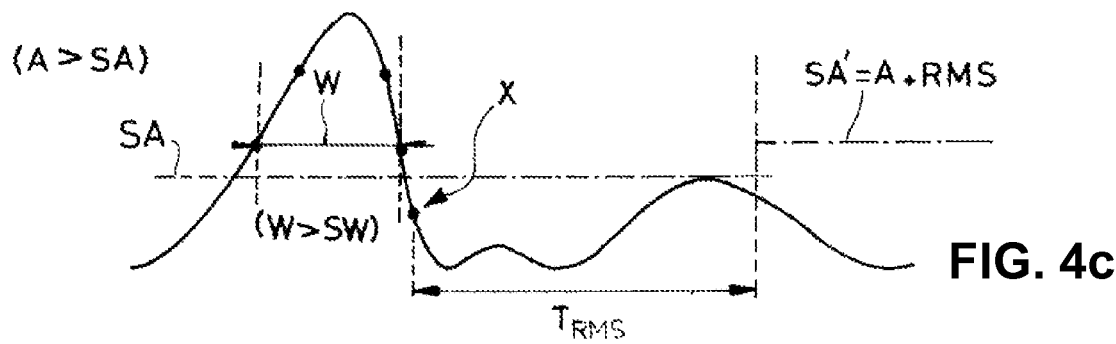

FIG. 4c illustrates the case wherein the signal amplitude A exceeds the amplitude threshold SA for a period W greater than the width threshold SW. In this case, it is considered that there is QRS detection (hence an output '1 is' delivered by comparator 30). Note that this detection signal is delivered with a delay relative to the start of the peak, a delay equal to the number of samples required to reach the width threshold SW. But this delay is relatively small: when the SW threshold is crossed, the signal is delivered by comparator 30.

Once the width threshold SW is reached, the algorithm then waits until the amplitude A falls below the threshold SA (e.g., the sample designated X in FIG. 4c). The calculation of the noise level is then triggered during the prescribed duration $T_{RMS}$ ($T_{RMS}$=32 ms). During all the duration $T_{RMS}$ of the calculation of noise level, the amplitude threshold SA is maintained at its previous value. At the end of the calculation, the amplitude threshold is automatically updated, from the value SA to the value SA'=$A_0$+RMS ($A_0$ being the base threshold, and RMS being the value of noise level which has just been calculated).

Figure 4D:
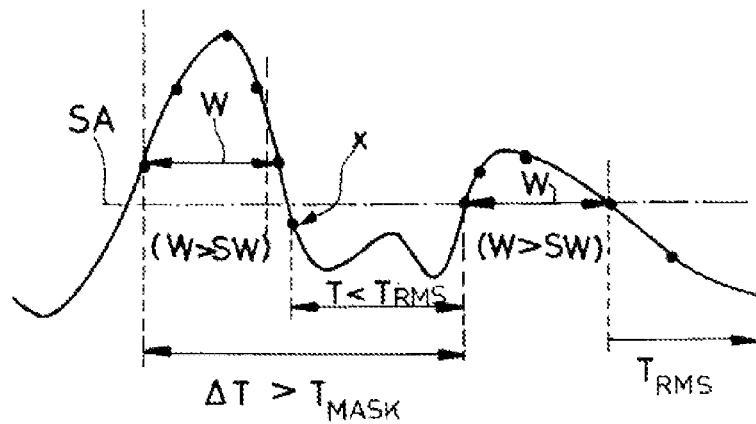

Finally, FIG. 4d illustrates a configuration wherein two close peaks are successively detected, with the start time of the second peak being located in a time interval ΔT of the beginning of the first peak. In this case:

If ΔT is below a predetermined period $T_{MASK}$, the two successive peaks are considered as a single peak, and only one QRS detection signal is output (i.e., the two close peaks are considered as a single QRS complex);

If, however, the second peak is detected with ΔT>$T_{MASK}$, then the two peaks are considered as two separate peaks, representing two distinct QRS complexes;

Furthermore, if the beginning of the second peak is detected before the end of the $T_{RMS}$ calculation of the noise level, then this noise calculation is canceled and the amplitude threshold SA remains unchanged. The calculation of the noise level will, however, be performed after the end second amplitude peak.

The detection technique according to the present invention was tested on acquired data for twenty patients in the Sorin CRM database having implanted devices whose ECG waveforms contained significant noise and thus reflected the highest rate of false positive detections in the Sorin CRM database. With conventional detection systems, the average rate of detection of false positives (oversensing), that is, the ratio of the number of amplitude peaks wrongly detected as QRS, compared to the total number of indicators of output peak detection delivered, was about 80%. With the present invention applied as described in the foregoing embodiment, the average rate of detection of false positives was reduced to about 18%, a decrease of more than four times the number of false detections, other things being equal.

One skilled in the art will understand that the present invention is not limited by, and may be practice by other than the foregoing embodiments described, which are presented for purposes of illustration and not of limitation.

The invention claimed is:

1. An active implantable medical device, comprising means for collecting, amplifying, prefiltering and converting from analog-to-digital an endocardial signal, means for digitally processing and analyzing the digitized endocardial signal, and for delivering an indicator of signal peak detection representative of a presence of a QRS complex in the endocardial signal, wherein the digitized endocardiac signal has an amplitude, the means for digital processing and analyzing comprises a double threshold comparator, having as an input said digitized endocardial signal, a peak amplitude threshold and a peak width threshold and having as an output said indicator of peak detection in response to, cumulatively:

the digitized endocardiac signal amplitude exceeding said peak amplitude threshold; and said peak amplitude threshold is exceeded for a period greater than said peak width threshold;

wherein said peak amplitude threshold is a variable adaptive threshold, and wherein the means for digitally processing and analyzing further comprises:

means for determining said peak amplitude threshold, by combining a predetermined base threshold and a variable value of noise level of the input endocardial signal; and means for determining said variable value of noise level based upon an energy (root mean square (RMS)) of the noise present in the input signal outside of the periods of said digitized endocardial signal amplitude exceeding said peak amplitude threshold.

2. The device of claim 1, wherein the means for determining said variable value of noise level further comprises means for calculating an energy of the endocardial input signal during a predetermined computing period during which the digitized endocardial signal amplitude does not exceed said peak amplitude threshold.

3. The device of claim 2, further comprising means for inhibiting and resetting the means determining the variable value of noise level in response said digitized endocardial signal amplitude exceeding said peak amplitude threshold before expiration of said predetermined computing period.

4. The device of claim 1, wherein said peak width threshold is a fixed predetermined threshold.

5. The device of claim 1, wherein the means for digital processing and analyzing further comprises:

A low-pass filter, for filtering said input endocardial signal.

6. The device of claim 5, wherein the means for digital processing and analyzing further comprises:

A high-pass filter and a rectifier, for filtering and rectifying the signal applied to the low-pass filter.

* * * * *